US010610708B2

(12) United States Patent
Awiszus et al.

(10) Patent No.: US 10,610,708 B2
(45) Date of Patent: Apr. 7, 2020

(54) INDICATING HAZARDOUS EXPOSURE IN A SUPPLIED AIR RESPIRATOR SYSTEM

(71) Applicant: 3M INNOVATIVE PROPERTIES COMPANY, St. Paul, MN (US)

(72) Inventors: Steven T. Awiszus, Woodbury, MN (US); Kiran S. Kanukurthy, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/190,564

(22) Filed: Jun. 23, 2016

(65) Prior Publication Data

US 2017/0368381 A1    Dec. 28, 2017

(51) Int. Cl.
*A62B 9/00* (2006.01)
*A42B 3/04* (2006.01)
(Continued)

(52) U.S. Cl.
CPC .............. *A62B 9/006* (2013.01); *A42B 3/046* (2013.01); *A42B 3/0453* (2013.01);
(Continued)

(58) Field of Classification Search
CPC ......... A42B 3/222; A42B 3/223; A42B 3/224; A42B 3/22; A42B 3/24; A62B 18/082;
(Continued)

(56) References Cited

U.S. PATENT DOCUMENTS 3,362,403 A * 1/1968 Fleming .................... A42B 3/12
128/201.24
4,549,541 A * 10/1985 Sundahl .................... A42B 3/08
128/201.19
(Continued)

FOREIGN PATENT DOCUMENTS

CN     105635085         1/2016
DE     102015001513 A1 * 3/2016 ............. A42B 3/224
(Continued)

OTHER PUBLICATIONS

New York Times article ""Pogonip" in Pittsburg Air" published Jan. 12, 1910.*

(Continued)

*Primary Examiner* — Kathryn E Ditmer
(74) *Attorney, Agent, or Firm* — Christopher D. Karlen (57) ABSTRACT

An exposure-indicating supplied air respirator system comprises a head top, a clean air supply source and a portable personal communication hub. The head top comprises a visor that is sized to fit over at least a user's nose and mouth, a position sensor secured to the head top, and a head top communication module. The clean air supply source is connected to the head top that supplies clean air to the interior of the head top. The position sensor detects whether the visor is in a closed position or in an open position and the head top communication module communicates the visor position to the personal communication hub. If the personal communication hub receives a signal indicating the presence of a hazard, and if the visor is in an open position, an alert is generated.

32 Claims, 5 Drawing Sheets

(51) Int. Cl.
*A42B 3/22* (2006.01)
*A62B 18/04* (2006.01)
*A62B 18/00* (2006.01)
*A62B 27/00* (2006.01)

(52) U.S. Cl.
CPC ............ *A42B 3/0466* (2013.01); *A42B 3/225* (2013.01); *A62B 9/00* (2013.01); *A62B 18/00* (2013.01); *A62B 18/045* (2013.01); *A62B 27/00* (2013.01)

(58) Field of Classification Search
CPC ......... A62B 18/00; A62B 18/04; A62B 18/08; A62B 17/04; A62B 17/006; A61M 16/0627
See application file for complete search history.

(56) References Cited

U.S. PATENT DOCUMENTS

| | | | |
|---|---|---|---|
| 4,619,255 A * | 10/1986 | Spinosa | A62B 7/14 128/202.27 |
| 4,907,296 A | 3/1990 | Blecha | |
| 5,189,735 A | 3/1993 | Corona | |
| 5,245,994 A * | 9/1993 | Chang | A62B 18/04 128/201.23 |
| 5,267,708 A | 12/1993 | Monson et al. | |
| 5,666,949 A | 9/1997 | Debe | |
| 5,796,341 A * | 8/1998 | Stratiotis | F16P 1/00 307/326 |
| 5,990,793 A | 11/1999 | Bieback | |
| 6,186,140 B1 | 2/2001 | Hoague | |
| 6,370,700 B1 | 4/2002 | Arion | |
| 6,456,199 B1 | 9/2002 | Michael | |
| 6,472,988 B1 | 10/2002 | Feld | |
| 6,715,150 B1 | 4/2004 | Potin | |
| 6,732,733 B1 | 5/2004 | Brostrom et al. | |
| 6,734,393 B1 | 5/2004 | Friedl | |
| 6,887,293 B1 | 5/2005 | Abad | |
| 7,019,652 B2 | 3/2006 | Richardson | |
| 7,080,414 B1 * | 7/2006 | Montero | A42B 3/224 2/424 |
| 7,234,462 B2 | 6/2007 | Palazzotto et al. | |
| 7,358,448 B2 | 4/2008 | Auray et al. | |
| 7,592,911 B1 | 9/2009 | Hudgens | |
| 7,628,443 B2 | 12/2009 | Krajenke | |
| 7,768,409 B2 | 8/2010 | Parias | |
| 7,792,615 B2 * | 9/2010 | Aimar | G01C 23/00 701/11 |
| 8,120,857 B2 | 2/2012 | Hedges et al. | |
| 8,294,580 B2 | 10/2012 | Witwer | |
| 8,316,850 B2 * | 11/2012 | Grilliot | A62B 9/006 128/201.25 |
| 8,821,621 B2 | 9/2014 | Dwyer et al. | |
| 8,823,609 B2 | 9/2014 | Furumiya | |
| 9,486,027 B2 | 11/2016 | Dey et al. | |
| 2003/0000001 A1 * | 1/2003 | McDonald | A62B 18/02 2/6.3 |
| 2004/0004547 A1 | 1/2004 | Appelt | |
| 2004/0100384 A1 | 5/2004 | Chen | |
| 2004/0182385 A1 * | 9/2004 | Uusitalo | A42B 3/0433 128/201.24 |
| 2004/0224293 A1 | 11/2004 | Penning et al. | |
| 2005/0114154 A1 | 5/2005 | Wolkowicz | |
| 2006/0044140 A1 | 3/2006 | Berg | |
| 2006/0085367 A1 | 4/2006 | Genovese | |
| 2006/0125623 A1 | 6/2006 | Appelt | |
| 2006/0162036 A1 | 7/2006 | McCalla | |
| 2006/0216956 A1 | 9/2006 | Forell et al. | |
| 2006/0238877 A1 | 10/2006 | Ashkenazi et al. | |
| 2007/0078528 A1 | 4/2007 | Anke | |
| 2007/0101995 A1 * | 5/2007 | Chornyj | A62B 7/02 128/205.22 |
| 2008/0018472 A1 | 1/2008 | Dasilva | |
| 2008/0021919 A1 | 1/2008 | Kaartinen | |
| 2008/0241805 A1 | 10/2008 | Schantz | |
| 2008/0302360 A1 * | 12/2008 | Chambers | A62B 9/02 128/202.13 |
| 2009/0125460 A1 | 5/2009 | Hewison | |
| 2009/0210989 A1 | 8/2009 | Becker | |
| 2009/0231423 A1 | 9/2009 | Becker | |
| 2009/0303588 A1 | 12/2009 | Charlesworth | |
| 2010/0064405 A1 | 3/2010 | McGovern | |
| 2010/0095439 A1 | 4/2010 | Nolan et al. | |
| 2010/0102970 A1 | 4/2010 | Hertz | |
| 2010/0107292 A1 * | 5/2010 | Chevallier | A42B 3/228 2/6.2 |
| 2010/0108067 A1 * | 5/2010 | Walker | A62B 17/04 128/205.24 |
| 2010/0132085 A1 | 6/2010 | Beaudet | |
| 2010/0265169 A1 * | 10/2010 | Baudou | A42B 3/0433 345/156 |
| 2011/0048416 A1 * | 3/2011 | Brace | A42B 3/288 128/201.24 |
| 2011/0056496 A1 * | 3/2011 | Tilley | A62B 7/10 128/205.27 |
| 2011/0227700 A1 | 9/2011 | Hamerly | |
| 2011/0314594 A1 | 12/2011 | Rogers et al. | |
| 2012/0084904 A1 | 4/2012 | Paulson | |
| 2012/0143526 A1 | 6/2012 | Benzel | |
| 2012/0223833 A1 | 9/2012 | Thomas et al. | |
| 2013/0031699 A1 | 2/2013 | Gafforio et al. | |
| 2013/0063550 A1 | 3/2013 | Ritchey | |
| 2013/0092164 A1 * | 4/2013 | Curran | A62B 7/10 128/204.21 |
| 2013/0139816 A1 | 6/2013 | Proctor | |
| 2013/0144130 A1 | 6/2013 | Russell | |
| 2013/0182414 A1 | 7/2013 | Fedewa et al. | |
| 2013/0291271 A1 | 11/2013 | Becker | |
| 2014/0319217 A1 | 10/2014 | Elefante | |
| 2015/0010158 A1 | 1/2015 | Broadley | |
| 2015/0109129 A1 | 4/2015 | Merril et al. | |
| 2015/0181972 A1 * | 7/2015 | Djerassi | A42B 3/224 2/424 |
| 2016/0018278 A1 | 1/2016 | Jeter | |
| 2016/0044276 A1 | 2/2016 | Shearman et al. | |
| 2016/0073722 A1 * | 3/2016 | Eustace | A42B 3/0466 340/539.13 |
| 2016/0085077 A1 | 3/2016 | Milea et al. | |
| 2016/0106174 A1 | 4/2016 | Chung | |
| 2016/0199674 A1 | 7/2016 | Johnson | |
| 2016/0210838 A1 | 7/2016 | Yan et al. | |
| 2016/0227866 A1 | 8/2016 | Tal | |
| 2016/0355262 A1 * | 12/2016 | Sharma | A62B 7/14 |
| 2017/0022807 A1 * | 1/2017 | Dursun | E21B 41/0021 |
| 2017/0032598 A1 | 2/2017 | Brioschi et al. | |
| 2017/0052000 A1 | 2/2017 | White et al. | |
| 2017/0273385 A1 | 9/2017 | Scheller | |
| 2017/0325534 A1 | 11/2017 | Noordzij et al. | |
| 2017/0330444 A1 | 11/2017 | M R | |
| 2019/0150546 A1 | 5/2019 | Egeland et al. | |

FOREIGN PATENT DOCUMENTS

| | | |
|---|---|---|
| GB | 2409961 | 7/2005 |
| JP | H10-262942 | 10/1998 |
| JP | H11-197159 | 7/1999 |
| JP | 2002-015107 | 1/2002 |
| JP | 2003-014847 | 1/2003 |
| JP | 2005-216137 | 8/2005 |
| JP | 2013-257638 | 12/2013 |
| JP | 2014-241119 | 12/2014 |
| KR | 2009-0123644 | 12/2009 |
| KR | 2013-0005424 | 9/2013 |
| KR | 10-2015-0102328 | 9/2015 |
| KR | 10-2015-0006350 | 1/2016 |
| RU | 2532801 | 11/2014 |
| RU | 2552996 | 6/2015 |
| RU | 162541 | 6/2016 |
| SU | 888993 | 12/1981 |
| WO | WO 95/21334 | 8/1995 |

(56) References Cited

FOREIGN PATENT DOCUMENTS

WO  WO 2009/141474  11/2009
WO  WO 2016/089708  6/2016

OTHER PUBLICATIONS

Sandulescu, "Wearable System for Stress Monitoring of Firefighters in Special Missions", The $5^{th}$ IEEE International Conference on E-Health and Bioengineering—EHB 2015, Nov. 19-21, 2015, pp. 1-4.
Machine Learning from Wikipedia, the free encyclopedia, retrieved from the internet Mar. 16, 2016, pp. 1-13.
"Modeling Human Performance in Chemical Protective Suits", Murray, 2010, Proceedings of the 2010 Industrial Engineering Research Conference.
"Outbreak Agent: Intelligent Wearable Technology for Hazardous Environments", Rogers, 1997, IEEE, 0-7803-4053, pp. 3198-3203.
"Artificial Intelligence" Russell, 2003, Prentice Hall.
"Evaluating the Physiological Performance of a Liquid Cooling Garment Used to Control Heat Stress in Hazmat Protective Ensembles", Semeniuk, 2005, Journal of ASTM International, Feb. 2005, vol. 2, No. 2.
U.S. Appl. No. 15/631,950, OA dated Nov. 27, 2017.
U.S. Appl. No. 15/190,564, Response to OA dated Nov. 27, 2017, Response dated Feb. 27, 2018.
U.S. Appl. No. 15/190,564, Applicant Initiated Interview Summary, Interview Agenda and Response, dated Feb. 27, 2018.
U.S. Appl. No. 15/631,870, OA dated Sep. 25, 2017.
U.S. Appl. No. 15/631,870, Response to OA dated Sep. 25, 2017, Response dated Dec. 22, 2017.
PCT/US2017/038846, International Search Report dated Sep. 13, 2017.
PCT/US2017/038846, Written Opinion of the ISA dated Sep. 13, 2017.
PCT/US2017/038983, International Search Report dated Sep. 28, 2017.
PCT/US2017/038983, Written Opinion of the ISA dated Sep. 28, 2017.
PCT/US2017/038983, Demand and Response to Written Opinion of the ISA dated Sep. 28, 2017, Response dated Dec. 19, 2017.
PCT/US2017/039041, International Search Report dated Sep. 28, 2017.
PCT/US2017/039041, Written Opinion of the ISA dated Sep. 28, 2017.
PCT/US2017/039041, Demand and Response to Written Opinion of the ISA dated Sep. 28, 2017, Response dated Dec. 19, 2017.
PCT/US2017/039003, International Search Report dated Sep. 14, 2017.
PCT/US2017/039003, Written Opinion of the ISA dated Sep. 14, 2017.
PCT/US2017/039015, International Search Report dated Sep. 21, 2017.
PCT/US2017/039015, Written Opinion of the ISA dated Sep. 21, 2017.
PCT/US2017/039030, International Search Report dated Aug. 10, 2017.
PCT/US2017/039030, Written Opinion of the ISA dated Aug. 10, 2017.
U.S. Appl. No. 15/631,950—Interview Summary dated Feb. 27, 2018.
U.S. Appl. No. 15/631,950—Response to Office Action dated Nov. 27, 2017, Response filed Feb. 27, 2018.
U.S. Appl. No. 15/631,950—Final Office Action dated Jun. 13, 2018.
U.S. Appl. No. 15/631,950—Interview Summary dated Jul. 16, 2018.
U.S. Appl. No. 15/631,950—Response to Final Office Action dated Jun. 13, 2018, Response filed Jul. 31, 2018.
U.S. Appl. No. 15/987,971—Office Action dated Aug. 27, 2018.
U.S. Appl. No. 15/987,971—Final Office Action dated Mar. 21, 2019.
U.S. Appl. No. 15/987,971—Response to Final Office Action dated Mar. 21, 2019; Response filed Apr. 22, 2019.

* cited by examiner

INDICATING HAZARDOUS EXPOSURE IN A SUPPLIED AIR RESPIRATOR SYSTEM

FIELD OF THE INVENTION

The present disclosure relates to the field of personal protective equipment. More specifically, the present disclosure relates to indicating exposure to a hazardous environment in a supplied air respiratory system.

BACKGROUND

When working in areas where there is known to be, or there is a potential of there being, dusts, fumes, gases or other contaminants that are potentially hazardous or harmful to health, it is usual for a worker to use a respirator or a clean air supply source. While a large variety of respiratory devices are available, some commonly used devices include powered air purifying respirators (PAPR) and a self-contained breathing apparatus (SCBA). A PAPR typically includes a blower system comprising a fan powered by an electric motor for delivering a forced flow of air through a tube to a head top worn by a user. A PAPR typically includes a device (i.e., turbo) that draws ambient air through a filter, forces the air through a breathing tube and into a helmet or head top to provide filtered air to a user's breathing zone, around their nose or mouth. An SCBA provides clean air from a compressed air tank through a tube or hose to the interior of a head top worn by a user. In order for a user to benefit from a clean air supply source, it is important for the user to have a seal around the exterior of a head top or helmet worn by the user.

SUMMARY

The present disclosure provides a system and a method for ensuring that a user of a supplied air respirator system keeps the visor of head top or helmet closed at the proper times to ensure decreased exposure to contaminants in an environment. The present disclosure provides a method for detecting when the visor is in an open position in a hazardous environment and generating an alert when exposure has exceeded a determined threshold, thus increasing worker safety and alerting the worker or others to potentially dangerous situations. Proper and effective use of a supplied air respirator, as determined and alerted, by this system also improves facility, site, or OSHA regulatory compliance. The data gathered will provide context as to who is properly operating their respirator and at what time. The present invention can also provide the benefit of giving a local alert to a user to indicate exposure, instead of only providing a record of hazardous exposure after the fact. This allows a user to address the situation that may be causing or allowing hazardous exposure.

In one aspect, the present disclosure includes an exposure-indicating supplied air respirator system. The system comprises a head top, a clean air supply source and a portable communication hub. The head top comprises a visor that is sized to fit over at least a user's nose and mouth, a position sensor secured to the head top, and a head top communication module. The clean air supply source is connected to the head top that supplies clean air to the interior of the head top. The position sensor detects whether the visor is in a closed position or in an open position, and the head top communication module communicates the visor position to the personal communication hub. If the personal communication hub receives a signal indicating the presence of a hazard, and if the visor is in an open position, an alert is generated.

In another instance, the present disclosure includes an exposure-indicating head top system comprising a head top and a portable personal communication hub. The head top comprising a visor that is sized to fit over at least the user's nose and mouth, a position sensor secured to the head top, and a head top communication module. The position sensor detects whether the visor is in a closed position or in an open position, and the head top communication module communicates the visor position to the personal communication hub. If the personal communication hub receives a signal indicating the presence of a hazard, and if the visor is in an open position, an alert is generated.

In another instance, the present disclosure includes an integrated exposure-indicating head top. The head top comprises a visor that is sized to fit over at least the user's nose and mouth, a position sensor secured to the head top, and a head top communication module. The position sensor detects whether the visor is in a closed position or in an open position. If the head top communication module receives a signal indicating the presence of a hazard, and if the visor is in an open position, an alert is generated.

Additional features and components can be added to each of the systems described above.

In some instances the clean air supply source comprises at least one of: a powered air purifying respirator (PAPR) and a self-contained breathing apparatus (SCBA).

In some instances the position sensor comprises at least one of: an accelerometer, gyro, magnet, switch or air pressure sensor.

In some instances the system further comprises an environmental beacon, wherein the environmental beacon comprises the environmental sensor and a communication module.

In some instances, the environmental beacon communication module includes at least one of: RFID, Bluetooth and WiFi communication capabilities.

In some instances, the alarm comprises at least one of: tactile, vibration, audible, visual, heads-up display or radio frequency signal.

In some instances, the head top communication module includes at least one of: radio frequency identification (RFID), Bluetooth and WiFi communication capabilities.

In some instances the personal communication hub includes at least one of: RFID, Bluetooth and WiFi communication capabilities.

In some instances the signal indicating the presence of the hazard is a location signal.

In some instances the signal indicating the presence of the hazard is generated based on detection of a hazard by an environmental sensor.

In some instances the environmental sensor determines the presence of a hazard when a contaminant level exceeds a designated hazard threshold.

In some instances the designated hazard threshold is configurable by the user.

In some instances the designated hazard threshold is stored on at least one of the environmental sensor and the personal communication hub.

In some instances the alert is generated after the visor has been in an open position for a period of time exceeding a designated exposure threshold.

In some instances the exposure threshold is configurable by the user.

In some instances the exposure threshold is stored on at least one of the head top and the personal communication hub.

In some instances the personal communication hub can be worn or carried.

In some instances the head top further comprises a head detection sensor.

In some instances the alert is only generated if the head detection sensor detects that the head top is being worn by the user.

In some instances the position sensor detects if the visor is in a partially open position.

In some instances, the system further comprises a temperatures sensor on the interior of the head top.

The present disclosure further includes a method of alerting a person or a worker when hazardous exposure is detected. The method comprises providing a head top comprising: a visor that is sized to fit over at least the user's nose and mouth, a position sensor, and a head top communication module. The method further comprises detecting with the position sensor whether the visor is in an open or a closed position. The method further comprises detecting the presence of a hazard and generating an alert if the visor is in an open position and if a hazard is present.

In some instances the presence of the hazard is detected by an environmental sensor.

In some instances the environmental sensor determines the presence of a hazard when a contaminant level exceeds a designated hazard threshold.

In some instances the alert is generated after the visor has been in an open position for a period of time exceeding a designated exposure threshold.

In some instances the head top further comprises a head detection sensor, and wherein the alert is only generated if the head detection sensor detects that the head top is being worn by the user.

In some instances the method further comprises detecting if the visor is in a partially open position.

In some instances the head top further comprises a temperature sensor, wherein the temperature sensor detects the temperature in the interior of the head top.

BRIEF DESCRIPTION OF THE DRAWINGS

The invention may be more completely understood in consideration of the following detailed description of various embodiments of the invention in connection with the accompanying drawings, in which.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
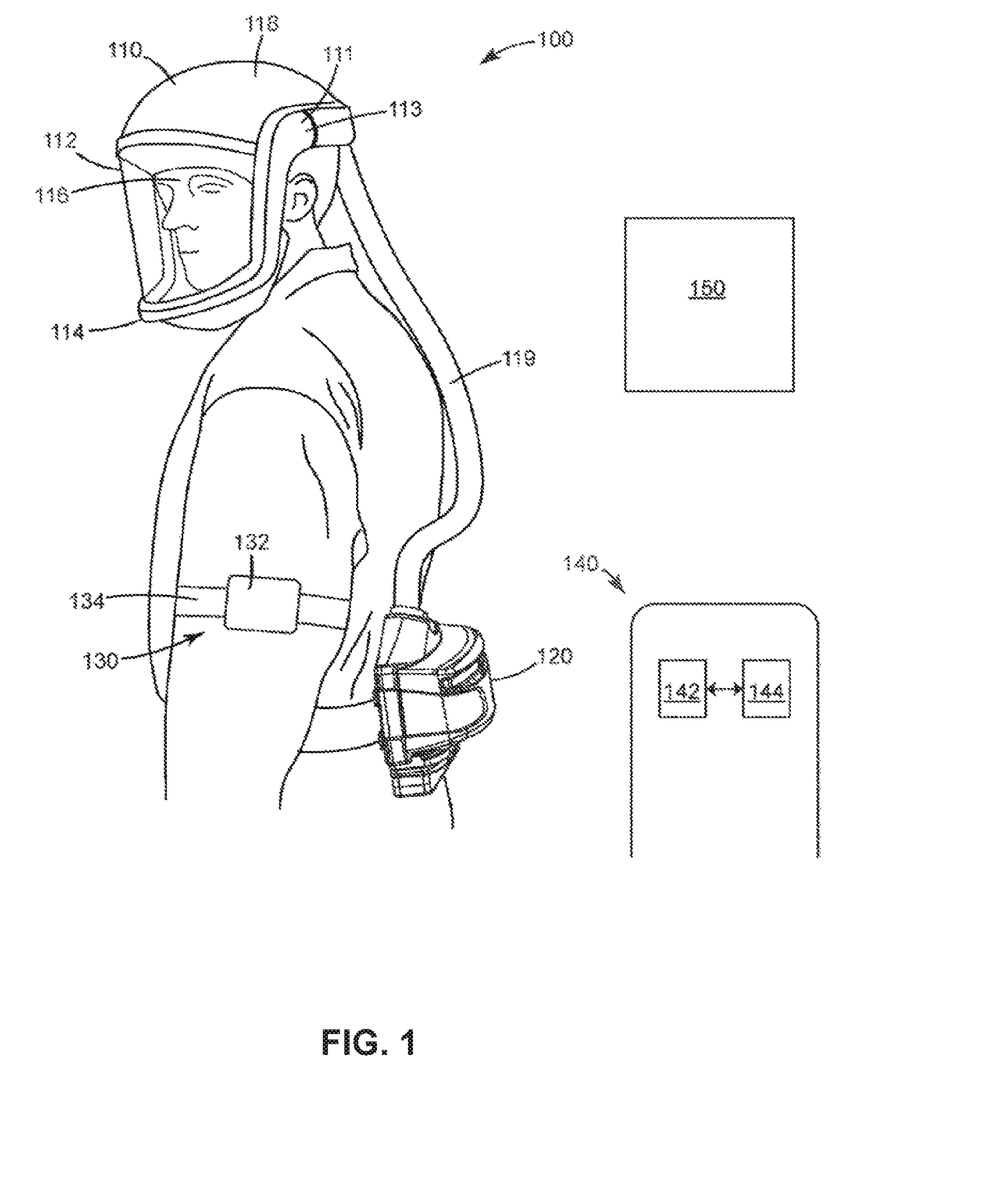
FIG. 1 is a system diagram of an exposure indicating supplied air respirator system.

FIG. 1 is a system diagram of an exposure indicating supplied air respirator system 100. System 100 includes head top 110, clean air supply source 120, communication hub 130, environmental beacon 140 and database 150. Head top 110 is connected to clean air supply source 120 by hose 119. Clean air supply source 120 can be any type of air supply source, such as a blower assembly for a powered air purifying respirator (PAPR), an air tank for a self-contained breathing apparatus (SCBA) or any other device that provides air to head top 110. In FIG. 1, clean air supply source 120 is a blower assembly for a PAPR. A PAPR is commonly used by individuals working in areas where there is known to be, or there is a potential of there being dusts, fumes or gases that are potentially harmful or hazardous to health. A PAPR typically includes blower assembly, including a fan driven by an electric motor for delivering a forced flow of air to the respirator user. The air is passed from the PAPR blower assembly through hose 119 to the interior of head top 110.

Head top 110 includes a visor 112 that is sized to fit over at least a user's nose and mouth. Visor 112 includes lens 116 which is secured to helmet 118 by the frame assembly 114. Head top also includes a position sensor 111 that senses the position of visor 112 relative to helmet 118 to determine if the visor is in an open position or in a closed position. In some instances, position sensor 111 may detect whether visor 112 is partially open, and if so, what measure (e.g., percent or degree) it is open. As an example, the position sensor 110 may be a gyroscope that computes angular yaw, pitch, and/or roll (in degrees or radians) of the visor 112 relative to the helmet 118. In another example, the position sensor 110 may be a magnet. A percent may be estimated respecting how open a visor 112 is in relation to the helmet 118 by determining the magnetic field strength or flux perceived by the position sensor 110. "Partially open" visor information can be used to denote that the user may be receiving eye and face protection for hazards while still receiving a reasonable amount of respiratory protection. This "partially open" visor state, if kept to short durations, can assist the user in face to face communications with other workers. Position sensor 111 can be a variety of types of sensors, for example, an accelerometer, gyro, magnet, switch, potentiometer, digital positioning sensor or air pressure sensor. Position sensor 111 can also be a combination of any of the sensors listed above, or any other types of sensors that can be used to detected the position of the visor 112 relative to the helmet 118.

Head top 110 may be supported on a user's head by a suspension (not shown).

Head top 110 may include other types of sensors. For example, head top 110 may include temperature sensor 113 that detects the ambient temperature in the interior of head top 110. Head top 110 may include other sensors such as an infrared head detection sensor positioned near the suspension of head top 110 to detect the presence of a head in head top 110, or in other words, to detect whether head top 110 is being worn at any given point in time. Head top 110 may also include other electronic components, such as a communication module, a power source, such as a battery, and a processing component. A communication module may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module in head top 110 can electronically interface with sensors, such as position sensor 111 or temperature sensor 113, such that it can transmit information from position sensor 111 or temperature sensor 113 to other electronic devices, including communication hub 130.

Communication hub 130 includes a processor, a communication module and a power supply. The communication module of communication hub 130 can include any desired communication capability, such as: RFID, Bluetooth, including any generations of Bluetooth technology, and WiFi communication capabilities. Communication hub 130 can also include any type of wireless communication capabilities, such as radio frequency or Zigbee communication.

Communication hub 130 includes electronics module 132 that has a power source, such as a battery, to provide power to both the processor and communication module. A rechargeable battery, such as a Lithium Ion battery, can provide a compact and long-life source of power. Communication hub 130 may be adapted to have electrical contacts exposed or accessible from the exterior of the hub to allow recharging the communication hub 130.

Communication hub 130 can include a processor that can receive, store and process information. For example, communication module in communication hub 130 may receive information from a communication module in head top 110 or directly from the position sensor 111 indicating the position of visor 112, whether visor 112 is open or closed, and at what time the visor 112 position changed. Any information collected by sensors and transmitted to or from communication hub 130 can be time stamped based on the time of an event that was sensed or detected, based on the time of transmission of information, or both. Processor in communication hub 130 can store this information and compare it with other information received. Other information received may include, for example, information from environmental beacon 140 and information from database 150. Communication hub 130 can further store rules, such as threshold information both for a length of time visor 112 is allowed to be in an open position before an alert is generated, and the level or type of contaminants that will trigger an alert. For example, when communication hub 130 receives information from environmental beacon 140 that there are no hazards present in the environment, the threshold for the visor 112 being in the open position may be infinite. If a hazard is present in the environment, then the threshold would be determined based upon the concern of the threat to the user. Radiation, dangerous gases, or toxic fumes would all require assignment of the threshold to be on the order of one second or less. Thresholds for head top temperature can be used to predict heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceed for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

A user's individual state of health could be a factor for adjusting the threshold. If a user is in a situation where donning or doffing could take a long time, battery notification threshold could be adjusted to allow for time to don and doff PPE.

Reaching different thresholds may result in triggering different types of alerts or alarms. For example, alarms may be informational (not requiring a user response), urgent (repeated and requiring a response or acknowledgement from a user), or emergency (requiring immediate action from a user.)

The type of alert or alarm can be tailored to the environment. Different types of alerts and alarms can be coupled together to get user attention. In some instances, a user may be able to "snooze" an alert or alarm.

Communication hub 130 may include a user interface, such as a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Communication hub 130 can be portable such that it can be carried or worn by a user. Communication hub 130 can also be personal, such that it is used by an individual and communicates with personal protective equipment (PPE) assigned to that individual. In FIG. 1, communication hub 130 is secured to a user using a strap 134. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

Environmental beacon 140 includes at least environmental sensor 142 which detects the presence of a hazard and communication module 144. Environmental sensor 142 may detect a variety of types of information about the area surrounding environmental beacon 140. For example, environmental sensor 142 may be a thermometer detecting temperature, a barometer detecting pressure, an accelerometer detecting movement or change in position, an air contaminant sensor for detecting potential harmful gases like carbon monoxide, or for detecting air-born contaminants or particulates such as smoke, soot, dust, mold, pesticides, solvents (e.g., isocyanates, ammonia, bleach, etc.), and volatile organic compounds (e.g., acetone, glycol ethers, benzene, methylene chloride, etc.). Environmental sensor 142 may detect, for example any common gasses detected by a four gas sensor, including: CO, O2, HS and Low Exposure Limit. In some instances, environmental sensor 142 may determine the presence of a hazard when a contaminant level exceeds a designated hazard threshold. In some instances, the designated hazard threshold is configurable by the user or operator of the system. In some instances, the designated hazard threshold is stored on at least one of the environmental sensor and the personal communication hub. In some instances, the designated hazard threshold is stored on database 150 and can be sent to communication hub 130 or environmental beacon 140 and stored locally on communication hub 130 or environmental beacon 140.

Environmental beacon communication module 144 is electronically connected to environmental sensor 142 to receive information from environmental sensor 142. Communication module 144 may include a variety of communication capabilities, such as: RFID, Bluetooth, including any generations of Bluetooth technology, and WiFi communication capabilities. Communication hub 130 can also include any type of wireless communication capabilities, such as radio frequency or Zigbee communication.

In some instances, environmental beacon 140 may store hazard information based on the location of environmental beacon 140. For example, if environmental beacon 140 is in an environment known to have physical hazards, such as the potential of flying objects, environmental beacon 140 may store such information and communicate the presence of a hazard based on the location of environmental beacon 140. In other instances, the signal indicating the presence of a hazard may be generated by environmental beacon 140 based on detection of a hazard by environmental sensor 142.

The system may also have an exposure threshold. An exposure threshold can be stored on any combination of database 150, communication hub 130, environmental beacon 140, and head top 110. A designated exposure threshold is the time threshold during which a visor 112 can be in the open position before an alert is generated. In other words, if the visor is in the open position for a period of time exceeding a designated exposure threshold, an alert may be generated. The designated exposure threshold may be configurable by a user or operator of the system. The designated exposure threshold may depend on personal factors related to the individual's health, age, or other demographic information, on the type of environment the user is in, and on the danger of the exposure to the hazard.

An alert can be generated in a variety of scenarios and in a variety of ways. For example, the alert may be generated by the communication hub 130 based on information received from head top 110 and environmental sensor 140. An alert may be in the form of an electronic signal transmitted to database 150 or to any other component of system 100. An alert may comprise one or more of the following types of signals: tactile, vibration, audible, visual, heads-up display or radio frequency signal.

Figure 2:
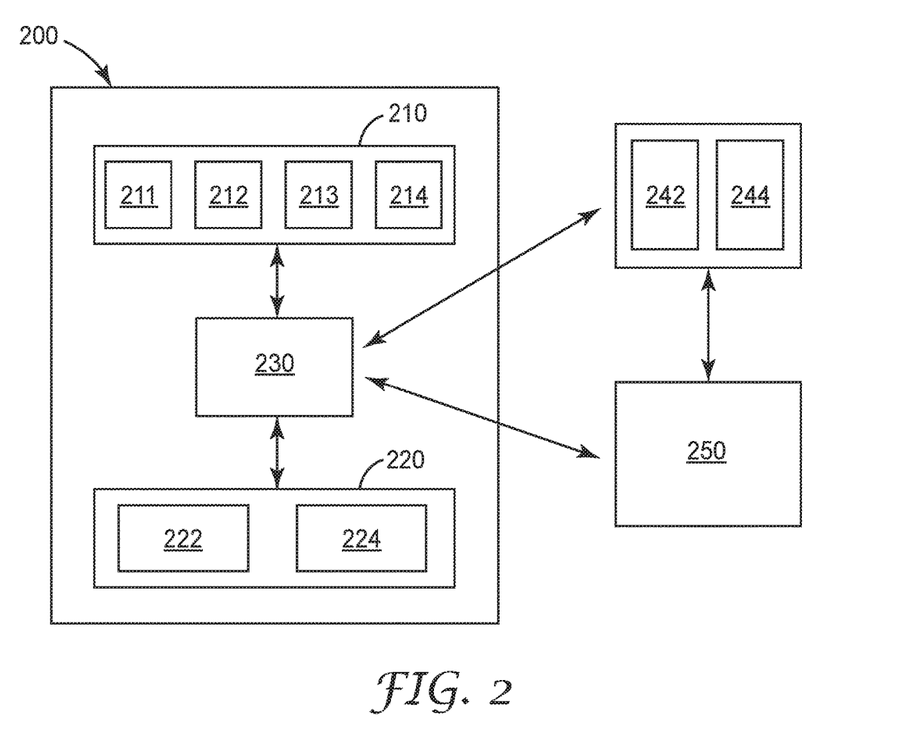
FIG. 2 is a block diagram of electronic components in an exposure indicating supplied air respirator system.

FIG. 2 is a block diagram of electronic components in an exposure indicating supplied air respirator system 200. Supplied air respirator system 200 communicates electronically with environmental beacon 240 and database 250 using any type of wireless communication mode, such as RFID, Bluetooth, including any generations of Bluetooth technology, and WiFi communication capabilities, radio frequency or Zigbee communication. Environmental beacon 240 and database 250 may communicate wirelessly or through wired connection.

Supplied air respirator system 200 includes head top 210, communication hub 230 and clean air supply source 220. Head top 210 includes several electronic components, such as position sensor 211, head detection sensor 212, temperature sensor 213, and communication module 214. While these are exemplary electronic components in head top 210, head top 210 may contain additional electronic components such as a processor to receive, store and process information from each of position sensor 211, head detection sensor 212, and temperature sensor 213, along with information received by communication module 214 from other devices. A processor may also control some or all of the sensors and communication module in head top 210. Other types of components, such as a battery or other power source and other types of sensors may also be included in head top 210.

Communication hub 230 communicates electronically with each of head top 210 and clean air supply source 220. Communication hub 230 can include any desired communication capability, such as: RFID, Bluetooth, including any generations of Bluetooth technology, and WiFi communication capabilities. Communication hub 230 can also include any type of wireless communication capabilities, such as radio frequency or Zigbee communication. Communication hub 230 may also communicate electronically with environmental beacon 240 and database 250.

Clean air supply source 220 includes a motor and fan assembly that provides a pressurized source of air to head top 210. Additionally, clean air supply source includes a processor 224 and a communication module 222. Processor 224 may interface with other components within clean air supply source 220. For example, processor 224 may interface with the battery or power source for clean air supply source 220 to determine how much battery life remains for the particular battery at any given point in time. Processor 224 may also communicate with the motor controlling fan speed, to determine how much air is being forced through the filter in clean air supply source 220, and therefore estimate remaining filter life. Data from the position sensor 211 may also be collected by the processor 224 to determine the measure that a visor is open or closed and/or the frequency that the visor changes status. Head detection sensor 212 and temperature sensor 213 data may also be transmitted to the processor 224 for additional analysis. In one example, if the head detection sensor 212 does not detect a head nor does the temperature sensor 213 indicate a rise in temperature and the position sensor 211 is open, then an alert will not be generated, transmitted, or stored. Processor 224 in clean air supply source 220 may track information such as flow rate, pressure drop across the filter, filter presence/identification on filter, battery run time, blower run time, filter run time, and whether the head top is a loose or tight fitting head top. Communication module 222 is in electrical communication with processor 224. Communication module 222 may include any desired communication capability, such as: RFID, Bluetooth, including any generations of Bluetooth technology, and WiFi communication capabilities. Communication module 222 can also include any type of wireless communication capabilities, such as radio frequency or Zigbee communication. Communication module can communicate wireless with communication hub 230. In some instances, communication module may communicate with other devices, such as environmental beacon 240 and database 250.

Figure 3:
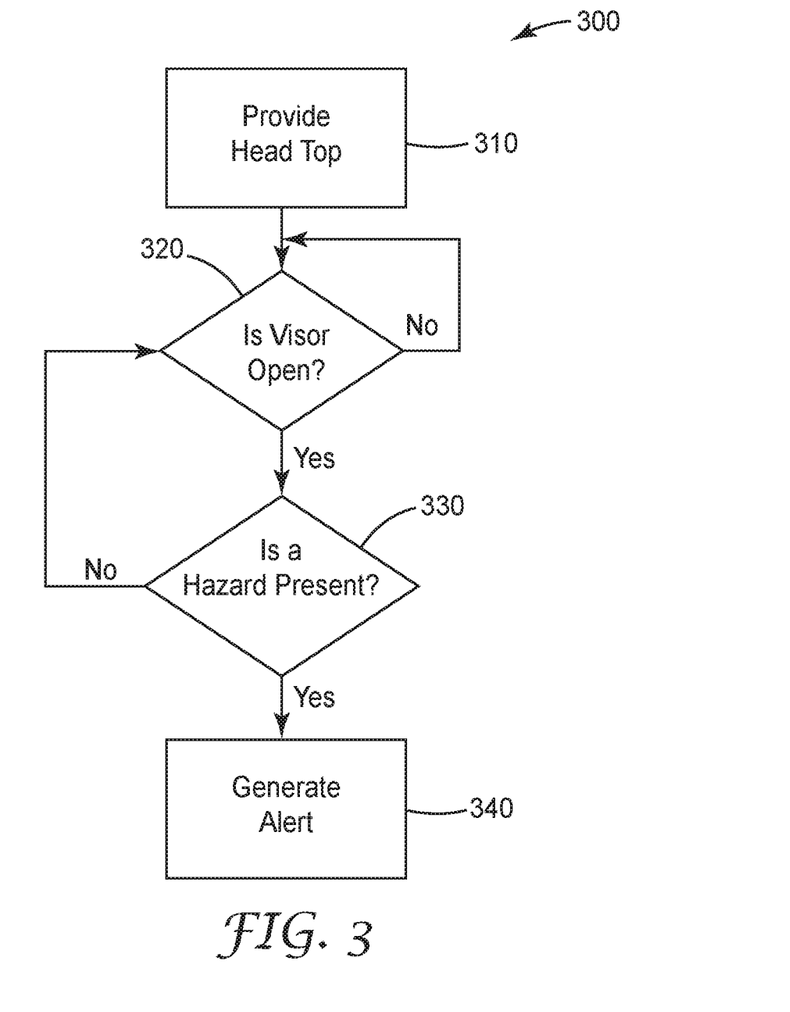
FIG. 3 is a flow chart associated with determining exposure.

FIG. 3 is a flow chart 300 associated with determining exposure, and indicating exposure to a user. While the steps shown in FIG. 3 are exemplary steps associated with the present disclosure, variations on the order of the steps, and additional steps, will be apparent to one of skill in the art upon reading the present disclosure.

Step 310 includes providing a head top to a user. A head top can include a visor that is sized to fit over at least user's nose and mouth, a position sensor, and a head top communication module. Various embodiments of head tops are described herein. In some instances, additional pieces of PPE or other devices may be provided, such as a clean air supply source, a personal communication hub, or any other desired component.

Step 320 includes detecting if the visor is in an open position. The visor position is detected by a position sensor in the head top. If the visor is in a closed position (or is not in an open position), step 320 is repeated. If the visor is in an open position, the system then queries whether a hazard is present in step 330. A hazard may be detected in a variety of ways, as described herein.

If a hazard is not detected in step 330, the system returns to step 320 to query whether the visor is open. If a hazard is detected in step 330, an alert is generated in step 340. A variety of types of alerts may be generated. For example, an alert may comprise one or more of the following types of signals: tactile, vibration, audible, visual, heads-up display or radio frequency signal. In some instances, an alert is not generated unless an exposure threshold and/or a hazard threshold is first met. Other variations of the steps shown are within the scope of the present disclosure. For example, in some instances the presence of the hazard is detected by an environmental sensor. In some instances, the environmental sensor determines the presence of a hazard when a contaminant level exceeds a designated hazard threshold.

In some instances, the alert is generated after the visor has been in an open position for a period of time exceeding a designated exposure threshold. In some instances, the head top further comprises a head detection sensor, and wherein the alert is only generated if the head detection sensor detects that the head top is being worn by the user. In some instances the system also detects if the visor is in a partially open position. In some instances, the head top further comprises a temperature sensor, wherein the temperature sensor detects the temperature in the interior of the head top.

Figure 4:
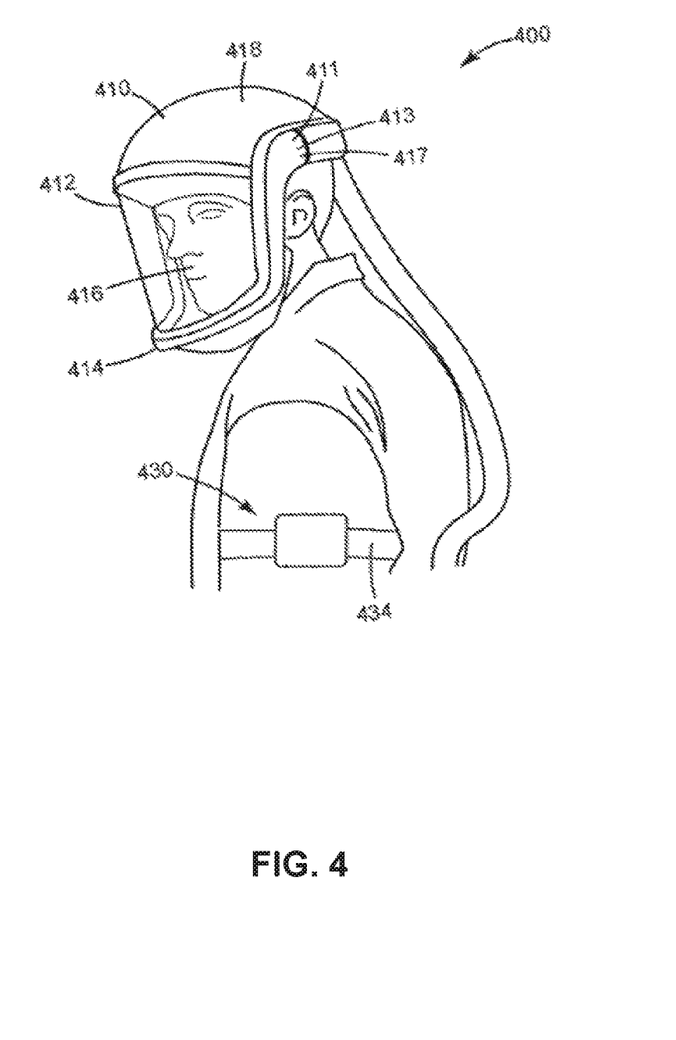
FIG. 4 is an exposure-indicating head top.

FIG. 4 is an exposure-indicating head top system 400 that includes a head top 410 with a visor 412 that is sized to fit over at least a user's nose and mouth. Visor 412 includes lens 416 which is secured to helmet 418 by the frame assembly 414. Head top also includes a position sensor 411 that senses the position of visor 412 relative to helmet 418 to determine if the visor is in an open position or in a closed position. In some instances, position sensor 411 may detect whether visor 412 is partially open, and if so, what measure (e.g., percent or degree) it is open. As an example, the position sensor 110 may be a gyroscope that computes angular yaw, pitch, and/or roll (in degrees or radians) of the visor 112 relative to the helmet 118. In another example, the position sensor 110 may be a magnet. A percent may be estimated respecting how open a visor 112 is in relation to the helmet 118 by determining the magnetic field strength or flux perceived by the position sensor 110. Position sensor 411 can be a variety of types of sensors, for example, an accelerometer, gyro, magnet, switch or air pressure sensor. Position sensor 411 can also be a combination of any of the sensors listed above, or any other types of sensors that can be used to detected the position of the visor 412 relative to the helmet 418.

Head top 410 may be supported on a user's head by a suspension (not shown).

Head top 410 may include other types of sensors. For example, head top 410 may include temperature sensor 413 that detects the ambient temperature in the interior of head top 410. Head top 410 may include other sensors such as an infrared head detection sensor positioned near the suspension of head top 410 to detected the presence of a head in head top 410, or in other words, to detect whether head top 410 is being worn at any given point in time. Head top 410 may also include other electronic components, such as a communication module 417, a power source, such as a battery, and a processing component. A communication module may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module can electronically interface with sensors, such as position sensor 411 or temperature sensor 413, such that it can transmit information from position sensor 411 or temperature sensor 413 to other electronic devices, including communication hub 430.

Communication hub 430 may include a user interface, such as a display, lights, buttons, keys (such as arrow or other indicator keys), and may be able to provide alerts to the user in a variety of ways, such as by sounding an alarm or vibrating. A user can set up WiFi parameters for the hub. The user interface includes, for example, a button, LED's and vibration ability.

Communication hub 430 can be portable such that it can be carried or worn by a user. Communication hub 430 can also be personal, such that it is used by an individual and communicates with personal protective equipment (PPE) assigned to that individual. In FIG. 4, communication hub 430 is secured to a user using a strap 434. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

Figure 5:
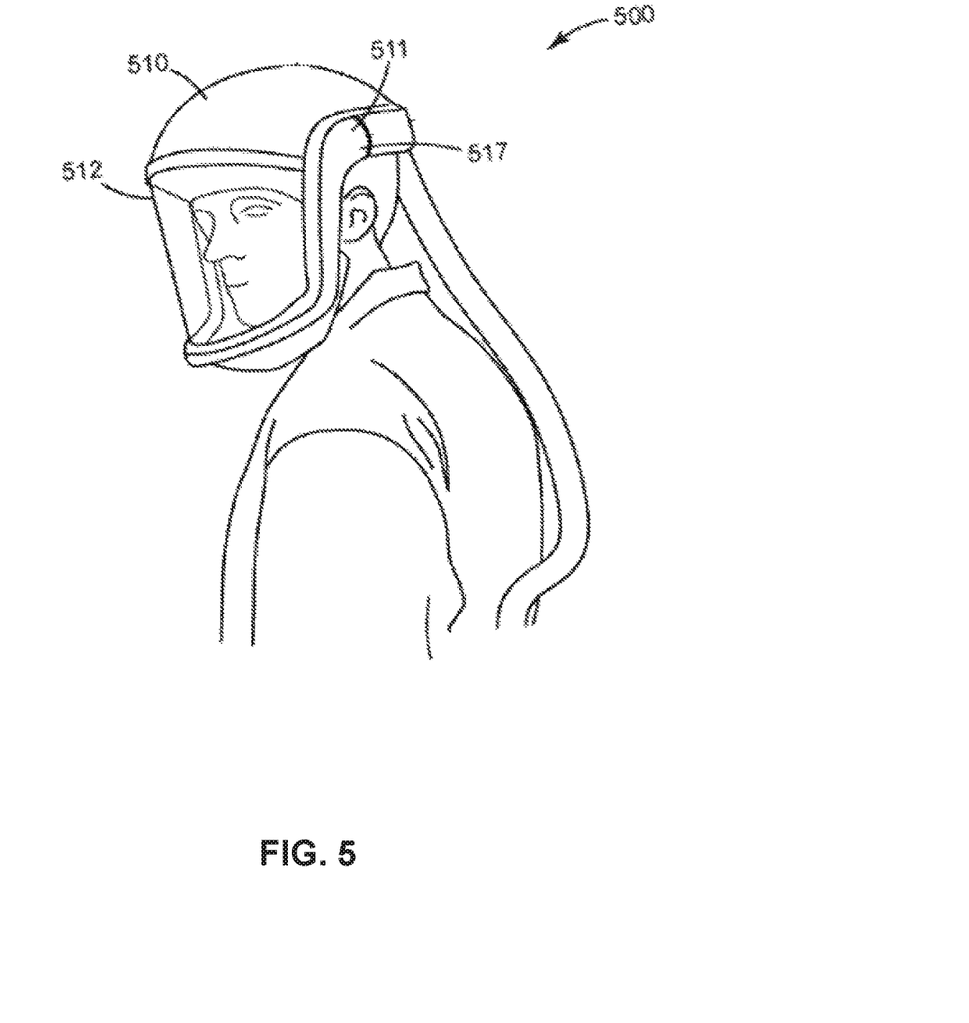
FIG. 5 is an exposure indicating head top and communication hub system.

FIG. 5 is an integrated exposure indicating head top and communication hub system 500. The system 500 includes a head top 510. Head top 510 includes at least a visor 512 that is sized to fit over at least the user's nose and mouth. Head top 510 further includes a position sensor 511 that detects whether the visor is in a closed position or in an open position. Head top 510 also includes communication module 517. If communication modules 517 receives a signal indicating the presence of a hazard, and if the visor 512 is in an open position, an alert as generated.

Communication module 517 may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module 517 may receive a signal indicating the presence of a hazard from a variety of other devices, such as an environmental beacon, a database or another communication device, such as a communication hub as described herein.

Example

Exposure-Indicating Supplied Air Respirator System

A head top 110 of a 3M™ Versaflo™ Heavy Industry PAPR Kit TR-300-HIK obtained from 3M Company of St. Paul, Minn. was modified to include a position sensor 111 between the visor 112 and helmet 118. The position sensor 110 was a LIS3MDL magnetometer obtained from ST Microelectronics. A communication hub 130 as described herein was wirelessly connected via Bluetooth to a processor within the head top that monitored the position sensor 111. A beacon 140 (Kontakt.io Smart Beach Two) obtained from Kontakt.io was programmed with a geographical location using global positioning system (GPS) coordinates and a radiation hazardous environmental condition. The visor 112 of the head top 110 was initially closed. The communication hub 130 wirelessly contacted the beacon 140 and determined that the head top was located in hazardous environment based upon the GPS location and radiation hazard status. The visor 112 was then opened and an alert was generated and was indicated with flashing light emitting diodes (LEDS) on the communication hub 130.

It will be appreciated that numerous and varied other arrangements may be readily devised by those skilled in the art without departing from the spirit and scope of the invention as claimed. For example, each of the communication modules in the various devices described throughout may be enabled to communicate as part of a larger network or with other devices to allow for a more intelligent infrastructure. Information gathered by various sensors may be combined with information from other sources, such as information captured through a video feed of a work space or an equipment maintenance space. In some instances, a portal configuration may be used such that if any of the systems described herein detect that a user or worker has exceeded a given threshold (whether high or low), the worker is prevented from physically gaining access to a particular work space or other area. Information gathered by the systems described herein can be used for further data analytics to determine compliance with various rules or regulations, and to improve safety processes. In some instances, a geo-location device, such as a global positioning system (GPS) may be incorporated into any of the systems described herein to provide user location. In some instances, the information collected by the systems and sensors described herein may be used to determine remaining service life of any PPE.

It will be appreciated that based on the above description, aspects of the disclosure include methods and systems for determining time of use (wear time) of articles, such as PPE articles, by determining if they satisfy at least one criterion.

Although the methods and systems of the present disclosure have been described with reference to specific exemplary embodiments, those of ordinary skill in the art will readily appreciate that changes and modifications may be made thereto without departing from the spirit and scope of the present disclosure.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

What is claimed is:

1. A wearable personal protective equipment system for a worker operating within a work environment that includes at least one contaminant hazardous to respiratory health of the worker, the system comprising:
    a head top configured to at least partially encompass the worker's head and defining an interior sealable space that is sealable from air exterior to the head top, the head top comprising:
        a visor that is sized to fit over at least the worker's eyes, nose and mouth, wherein the visor is configured to expose the interior sealable space defined by the head top to air external to the head top when the visor is in an open position and is configured to seal the interior sealable space defined by the head top from the air external to the head top when the visor is in a closed position in which the visor is positioned in front of at least the worker's eyes, nose, and mouth, and
        a position sensor secured to the head top and configured to output an indication of a position of the visor;
    a wearable powered air purifying respirator (PAPR) connected to the head top for supplying clean air to the interior sealable space defined by the head top, wherein the PAPR includes a blower configured to force the clean air to the head top;
    a hose configured to connect the PAPR to the head top to provide the clean air to the head top;
    an air contaminant sensor configured to detect a contaminant in the air external to the head top, wherein the contaminant is comprised of a material that is hazardous to respiratory health of the worker, and wherein the head top is configured such that the contaminant is breathable by the worker when the visor is in the open position and is prevented from contaminating the clean air within the interior sealable space defined by the head top when the visor is in the closed position; and
    at least one processor configured to:
        receive the indication of the position of the visor;
        determine, based on the indication of the position of the visor, whether the visor is in the closed position, a partially open position, or in the open position;
        determine whether a level of the contaminant in the air external to the head top is greater than a threshold contamination level; and
        responsive to determining that the level of the contaminant is greater than the threshold contamination level and that the visor is in the partially open position or the open position, generate an alert to the worker to indicate the level of the contaminant is greater than the threshold contamination level, the alert comprising at least one of a vibration, audible output, or light-emitted visual output.

2. The system of claim 1, wherein the position sensor comprises at least one of: an accelerometer, gyro, magnet, switch, or air pressure sensor.

3. The system of claim 1, further comprising an environmental beacon, wherein the environmental beacon comprises the air contaminant sensor and a communication module, wherein the communication module of the environmental beacon is configured to output an indication of the level of the contaminant to the at least one processor.

4. The system of claim 3, wherein the communication module of the environmental beacon includes wireless communication capabilities.

5. The system of claim 1, wherein the head top further comprises a communication module, wherein the position sensor is configured to output the indication of the position of the visor via the communication module of the head top, wherein the communication module of the head top includes wireless communication capabilities.

6. The system of claim 1, wherein the at least one processor includes a first processor and a second processor, wherein the head top includes the first processor, the system further comprising:
    a portable personal communication hub that includes the second processor and a communication module, wherein the communication module of the personal communication hub includes wireless communication capabilities,
    wherein the first processor is configured to:
        receive the indication of the position of the visor,
        determine whether the visor is in the closed position, the partially open position, or the open position, and
        output an indication of whether the visor is in the closed position, the partially open position, or the open position,
    wherein the second processor is configured to:
        receive, via the communication module of the personal communication hub, the indication of whether the visor is in the closed position, the partially open position, or the open position;
        receive, via the communication module of the personal communication hub, an indication of the level of the contaminant;
        determine whether the level of the contaminant is greater than the threshold contamination level, and
        generate the alert.

7. The system of claim 1, wherein the threshold contamination level is configurable by the worker.

8. The system of claim 1, further comprising a memory configured to store the threshold contamination level.

9. The system of claim 1, wherein the at least one processor is further configured to:
    determine an amount of time the visor is in the open position or the partially open position, and
    generate the alert in further response to determining that the amount of time is greater than a threshold amount of time.

10. The system of claim 9, further comprising a memory configured to store data indicating the threshold amount of time.

11. The system of claim 9, wherein the at least one processor is further configured to determine the threshold amount of time based at least in part on a threat to the respiratory health of the worker.

12. The system of claim 11, wherein the at least one processor is further configured to determine the threshold amount of time based at least in part on a type of the contaminant.

13. The system of claim 9,
    wherein the at least one processor is further configured to
        determine that the threshold amount of time is a first threshold amount of time in response to determining the visor is in a partially open position, and wherein the at least one processor is further configured to determine that the threshold amount of time is a second threshold amount of time in response to determining the visor is in the open position, the second threshold amount of time different than the first threshold amount of time.

14. The system of claim 9, wherein the at least one processor is further configured to determine a degree or a percentage that the visor is open, and wherein the at least one processor is further configured to determine the threshold amount of time based at least in part on the degree or the percentage that the visor is open.

15. The system of claim 1, wherein the head top further comprises a head detection sensor configured to detect whether the head top is being worn by the worker.

16. The system of claim 15, wherein the head detection sensor comprises a temperature sensor configured to detect an air temperature inside the head top, wherein the air temperature inside the head top indicates whether the head top is being worn by the worker.

17. The system of claim 1, further comprising a computing device that includes the at least one processor, wherein the computing device is physically separate from the head top and the PAPR, and wherein the computing device is communicatively coupled to at least one of the head top or the PAPR.

18. The system of claim 1, wherein the at least one processor is configured to, responsive to determining that the level of the contaminant is greater than the threshold contamination level and that the visor is in the open position, send data to at least one other computing device.

19. The system of claim 1, wherein the material that is hazardous to the respiratory health of the worker and that is detected by the air contaminant sensor as the contaminant in the air external to the top further comprises one or more of smoke, a mold, a pesticide, or a solvent.

20. The system of claim 1, wherein the material that is hazardous to the respiratory health of the worker and that is detected by the air contaminant sensor as the contaminant in the air external to the top further comprises a volatile organic compound.

21. The system of claim 1, wherein the material that is hazardous to the respiratory health of the worker and that is detected by the air contaminant sensor as the contaminant in the air external to the top further comprises a gas.

22. The system of claim 1, wherein the hose is coupled to the head top at a rear of the head top and delivers air to the head top via the rear of the head top, and wherein the rear of the head top is opposite the visor.

23. The system of claim 1, wherein the position sensor comprises a magnet.

24. The system of claim 23, wherein the indication of the position of the visor includes data indicative of a strength of a magnetic field generated by the magnet, and wherein the at least one processor is configured to determine whether the visor is in the closed position, the partially open position, or the open position based on the data indicative of the strength of the magnetic field.

25. A head top system for a worker operating within a work environment that includes at least one contaminant hazardous to respiratory health of the worker, the system comprising:
a head top configured to at least partially encompass the worker's head and defining an interior sealable space that is sealable from air exterior to the head top, the head top comprising:
a visor that is sized to fit over at least the worker's eyes, nose and mouth,
wherein the visor is configured to expose the interior sealable space defined by the head top to air external to the head top when the visor is in an open position and is configured to seal the interior sealable space defined by the head top from the air external to the head top when the visor is in a closed position in which the visor is positioned in front of at least the worker's eyes, nose, and mouth,
wherein the head top is configured to connect to a portable, wearable powered air purifying respirator (PAPR) via a hose at a rear of the head top, the rear of the head top being opposite the visor, and
wherein the head top is configured such that a contaminant is breathable by the worker when the visor is in the open position and is prevented from contaminating air within the interior sealable space defined by the head top when the visor is in the closed position, and
a position sensor secured to the head top and configured to output an indication of a position of the visor, and
a processor configured to:
receive the indication of the position of the visor;
receive an indication that air external to the head top is contaminated, wherein the contaminant is comprised of a material that is hazardous to respiratory health of the worker;
determine, based on the indication of the position of the visor, whether the visor is in the closed position, in a partially open position, or in the open position; and
responsive to receiving the indication that the air external to the head top is contaminated and determining that the visor is in the open position or the partially open position, generate an alert to the worker to indicate the level of the contaminant is greater than a threshold contamination level, the alert comprising at least one of a vibration, audible output, or light-emitted visual output.

26. The exposure-indicating head top system of claim 25, wherein the processor is configured to, responsive to determining that the level of the contaminant is greater than the threshold contamination level and that the visor is in the open position, send data to at least one other computing device.

27. An integrated exposure-indicating head top configured to at least partially encompass a worker's head and defining an interior sealable space that is sealable from air exterior to the head top, the head top configured to be worn by a worker operating within a work environment that includes at least one contaminant hazardous to respiratory health of the worker, the head top comprising:
a visor that is sized to fit over at least the worker's eyes, nose and mouth,
wherein the visor is configured to expose the interior sealable space defined by the head top to air external to the head top when the visor is in an open position and is configured to seal the interior sealable space defined by the head top from the air external to the head top when the visor is in a closed position in which the visor is positioned in front of at least the worker's eyes, nose, and mouth,
wherein the head top is configured to connect to a portable, wearable powered air purifying respirator (PAPR) via a hose at a rear of the head top, the rear of the head top opposite the visor, and wherein the head top is configured such that a contaminant is breathable by the worker when the visor is in the open position and is prevented from contaminating air within the interior sealable space defined by the head top when the visor is in the closed position, a position sensor secured to the head top configured to detect whether the visor is in the closed position, in a partially open position, or in the open position; and a processor configured to:
receive an indication that air external to the head top is contaminated; and
responsive to receiving the indication that the air external to the head top is contaminated and detecting that the visor is in the open position or the partially open position, generate an alert to indicate the level of the contaminant is greater than a threshold contamination level.

28. A wearable personal protective equipment system for a worker operating within a work environment that includes at least one contaminant hazardous to respiratory health of the worker, the system comprising:

a head top configured to at least partially encompass the worker's head and defining an interior sealable space that is sealable from air exterior to the head top, the head top comprising:
a visor that is sized to fit over at least the worker's eyes, nose and mouth, wherein the visor is configured to expose the interior sealable space defined by the head top to air external to the head top when the visor is in an open position and is configured to seal the interior sealable space defined by the head top from the air external to the head top when the visor is in a closed position in which the visor is positioned in front of at least the worker's eyes, nose, and mouth, and
a position sensor secured to the head top and configured to output an indication of a position of the visor;

a wearable powered air purifying respirator (PAPR) connected to the head top for supplying clean air to the interior sealable space defined by the head top, wherein the PAPR includes a blower configured to force the clean air to the head top;

a hose configured to connect the PAPR to the head top to provide the clean air to the head top;

an air contaminant sensor configured to detect a contaminant in the air external to the head top, wherein the contaminant is comprised of a material that is hazardous to respiratory health of the worker, and wherein the head top is configured such that the contaminant is breathable by the worker when the visor is in the open position and is prevented from contaminating the clean air within the interior sealable space defined by the head top when the visor is in the closed position; and at least one processor configured to:
receive the indication of the position of the visor;
determine, based on the indication of the position of the visor, whether the visor is in the closed position or in the open position;
determine an amount of time the visor is in the open position;
determine whether a level of the contaminant in the air external to the head top is greater than a threshold contamination level; and
responsive to determining that the level of the contaminant is greater than the threshold contamination level and that the amount of time the visor is in the open position satisfies a threshold amount of time, generate an alert to the worker to indicate the level of the contaminant is greater than the threshold contamination level, the alert comprising at least one of a vibration, audible output, or light-emitted visual output.

29. A method of alerting a person or a worker when hazardous exposure is detected, the method comprising:
outputting, by a position sensor of a head top that includes a visor sized to fit over at least a user's nose and mouth an indication of a position of the visor;
detecting, by an air contaminant sensor, a contaminant in air external to the head top;
determining, by at least one processor, based on the indication of the position of the visor, whether the visor is in an open, a partially open position, or a closed position;
determining, by the at least one processor, whether a level of the contaminant is greater than a threshold contamination level; and
responsive to determining that the level of the contaminant is greater than the threshold contamination level and that the visor is in the partially open position, generating, by the at least one processor, an alert.

30. The method of claim 29, wherein generating the alert is further responsive to determining, by the at least one processor, that the visor has been in the partially open position for a period of time exceeding a threshold amount of time.

31. The method of claim 29, further comprising:
determining, by the at least one processor and based on information received from a head detection sensor of the head top, whether the head top is being worn by the user, and
wherein generating the alert is further responsive to determining that the head top is being worn by the user.

32. The method of claim 29, further comprising detecting, by a temperature sensor of the head top, a temperature inside the head top.

* * * * *

UNITED STATES PATENT AND TRADEMARK OFFICE
CERTIFICATE OF CORRECTION

PATENT NO. : 10,610,708 B2
APPLICATION NO. : 15/190564
DATED : April 7, 2020
INVENTOR(S) : Steve Awiszus Page 1 of 1

It is certified that error appears in the above-identified patent and that said Letters Patent is hereby corrected as shown below:

In the Claims

Column 16, Line 41, Claim 26, before "system" delete "exposure-indicating head top".

Signed and Sealed this
Third Day of November, 2020

Andrei Iancu
*Director of the United States Patent and Trademark Office*